(12) United States Patent
Olenik et al.

(10) Patent No.: US 8,324,392 B2
(45) Date of Patent: Dec. 4, 2012

(54) SOLID FORM OF 4-[[(6-CHLOROPYRIDIN-3-YL)METHYL](2,2-DIFLUOROETHYL)AMINO]FURAN-2(5H)-ONE

(75) Inventors: Britta Olenik, Bottrop (DE); Robert Velten, Langenfeld (DE); Peter Jeschke, Bergisch Gladbach (DE); Norbert Lui, Odenthal (DE); Christian Funke, Leichlingen (DE); Wolfgang Wirth, Bergisch Gladbach (DE)

(73) Assignee: Bayer Cropscience AG, Monheim (DE)

( * ) Notice: Subject to any disclaimer, the term of this patent is extended or adjusted under 35 U.S.C. 154(b) by 90 days.

(21) Appl. No.: 12/910,201

(22) Filed: Oct. 22, 2010

(65) Prior Publication Data

US 2011/0130288 A1    Jun. 2, 2011

Related U.S. Application Data

(60) Provisional application No. 61/255,600, filed on Oct. 28, 2009.

(30) Foreign Application Priority Data

Oct. 26, 2009  (EP) .................................... 09174046

(51) Int. Cl.
*C07D 213/62* (2006.01)
*A61K 31/44* (2006.01)

(52) U.S. Cl. ........................ 546/300; 514/350

(58) Field of Classification Search .................. None
See application file for complete search history.

(56) References Cited

U.S. PATENT DOCUMENTS

| 7,417,150 B2 | 8/2008 | Jeschke et al. |
| 2008/0280953 A1 | 11/2008 | Gorgens et al. |
| 2009/0253749 A1 | 10/2009 | Jeschke et al. |
| 2010/0190990 A1 | 7/2010 | Lui et al. |

FOREIGN PATENT DOCUMENTS

| EP | 0539588 | 5/1993 |
| WO | 02085870 | 10/2002 |
| WO | 2006/037475 | 4/2006 |
| WO | 2007/115644 | 10/2007 |
| WO | 2009/036899 | 3/2009 |

OTHER PUBLICATIONS

Brittain, H., ed. Polymorphism in Pharmaceutical Solids, 2009 Informa Health Care, excerpt, pp. 318-335.*

* cited by examiner

*Primary Examiner* — Janet Andres
*Assistant Examiner* — Heidi Reese
(74) *Attorney, Agent, or Firm* — Baker Donelson Bearman, Caldwell & Berkowitz, PC

(57) ABSTRACT

The present invention relates to a novel solid form of 4-[[(6-chloropyridin-3-yl)methyl](2,2-difluoroethyl)amino]furan-2(5H)-one, to processes for its preparation and to its use in agrochemical preparations.

13 Claims, 6 Drawing Sheets

SOLID FORM OF 4-[[(6-CHLOROPYRIDIN-3-YL)METHYL](2,2-DIFLUOROETHYL)AMINO]FURAN-2(5H)-ONE

CROSS REFERENCE TO RELATED APPLICATIONS

This application claims priority to European Application No. 09174046.4 filed Oct. 26, 2009 and U.S. Application No. 61/255,600 filed Oct. 28, 2009, the entire contents of which are incorporated herein by reference in their entireties.

BACKGROUND OF THE INVENTION

1. Field of the Invention

The present invention relates to a novel solid form of 4-[[(6-chloropyridin-3-yl)methyl](2,2-difluoroethyl)amino]furan-2(5H)-one, to a process for preparing this novel solid form and to its advantageous use for preparing stable use forms.

2. Description of Related Art

The compound 4-[[(6-chloropyridin-3-yl)methyl](2,2-difluoroethyl)amino]furan-2(5H)-one and methods for preparing this compound are known. It is also known that this compound has insecticidal and acaricidal action. Thus, for example, WO 2007/115644 describes for the first time the preparation of this compound and its use for controlling arthropods, in particular insects. Furthermore, the preparation of this compound has been described in WO2009/036899. It has now been found that the compound prepared by the known processes cannot be used in an economically relevant form, since the compound prepared by these processes is present in amorphous form. This becomes evident by the fact that it is not possible to determine a melting point. Melting points are always present if there is a long-range order, especially if a crystalline structure is present. Likewise, as can be seen from FIG. 1a, it is not possible to obtain a resolved X-ray powder diffractogram.

In particular, it is a disadvantage that the compound is highly viscous in the amorphous state and can therefore not be converted into formulations in which the active compound is present in solid (dry) form. Such economically important formulations are, for example, granules, encapsulated granules, tablets, water-dispersible granules, water-dispersible tablets, water-dispersible powders or water-dispersible powders for the treatment of seed, dust formulations, formulations in which the active compound is present in dispersed form, such as, for example: suspension concentrates, oil-based suspension concentrates, suspoemulsions or suspension concentrates for the treatment of seed. Formulations are of economical relevance, for example, when the active compounds to be used are particularly suitable for preparing formulations requiring the use of grinding processes, and/or when such formulations have good storage stability.

SUMMARY OF THE INVENTION

Surprisingly, we have now found a novel solid form of 4-[[(6-chloropyridin-3-yl)methyl](2,2-difluoroethyl)amino]furan-2(5H)-one which avoids the disadvantages mentioned above.

Accordingly, the invention relates to the novel solid form of the compound 4-[[(6-chloropyridin-3-yl)methyl](2,2-difluoroethyl)amino]furan-2(5H)-one which is characterized in that it has a melting point in the range from 65° C. to 75° C., in particular a melting point range of from 72° C. to 74° C., and/or in that the X-ray powder diffractogram of this compound has, at 25° C. and with Cu—Kα radiation (1.540598 Å) being used, at least 3 characteristical signals, in particular at least 4 or 6 characteristical signals and preferably all of the following characteristic 2Θ (2 theta) values:

| |
|---|
| 2Θ = 16.8° ± 0.2 |
| 2Θ = 17.8° ± 0.2 |
| 2Θ = 20.2° ± 0.2 |
| 2Θ = 21.7° ± 0.2 |
| 2Θ = 23.6° ± 0.2 |
| 2Θ = 23.9° ± 0.2 |
| 2Θ = 24.7° ± 0.2 |
| 2Θ = 25.3° ± 0.2 |

DETAILED DESCRIPTION OF A PREFERRED EMBODIMENT

According to the invention, the term "characteristical signal" means such signals (e.g. 2Θ (2 theta) values or IR- or Raman bands) which can be clearly distinguished from the background noise and which are characteristic for the measured compound.

Furthermore, the novel solid form has, corresponding to the characteristic 2 theta values, the lattice plane spacings "d" listed in Table 1.

TABLE 1

Characteristic 2 Theta values and lattice plane spacings "d" of the novel solid form of the compound 4-[[(6-chloropyridin-3-yl)methyl](2,2-difluoroethyl)amino]furan-2(5H)-one, determined by X-ray powder spectroscopy

| 2 θ | d [Å] |
|---|---|
| 16.8 ± 0.2 | 5.3 ± 0.1 |
| 17.8 ± 0.2 | 5.0 ± 0.1 |
| 20.2 ± 0.2 | 4.4 ± 0.1 |
| 21.7 ± 0.2 | 4.1 ± 0.1 |
| 23.6 ± 0.2 | 3.8 ± 0.1 |
| 23.9 ± 0.2 | 3.7 ± 0.1 |
| 24.7 ± 0.2 | 3.6 ± 0.1 |
| 25.3 ± 0.2 | 3.5 ± 0.1 |

Figure 1A:
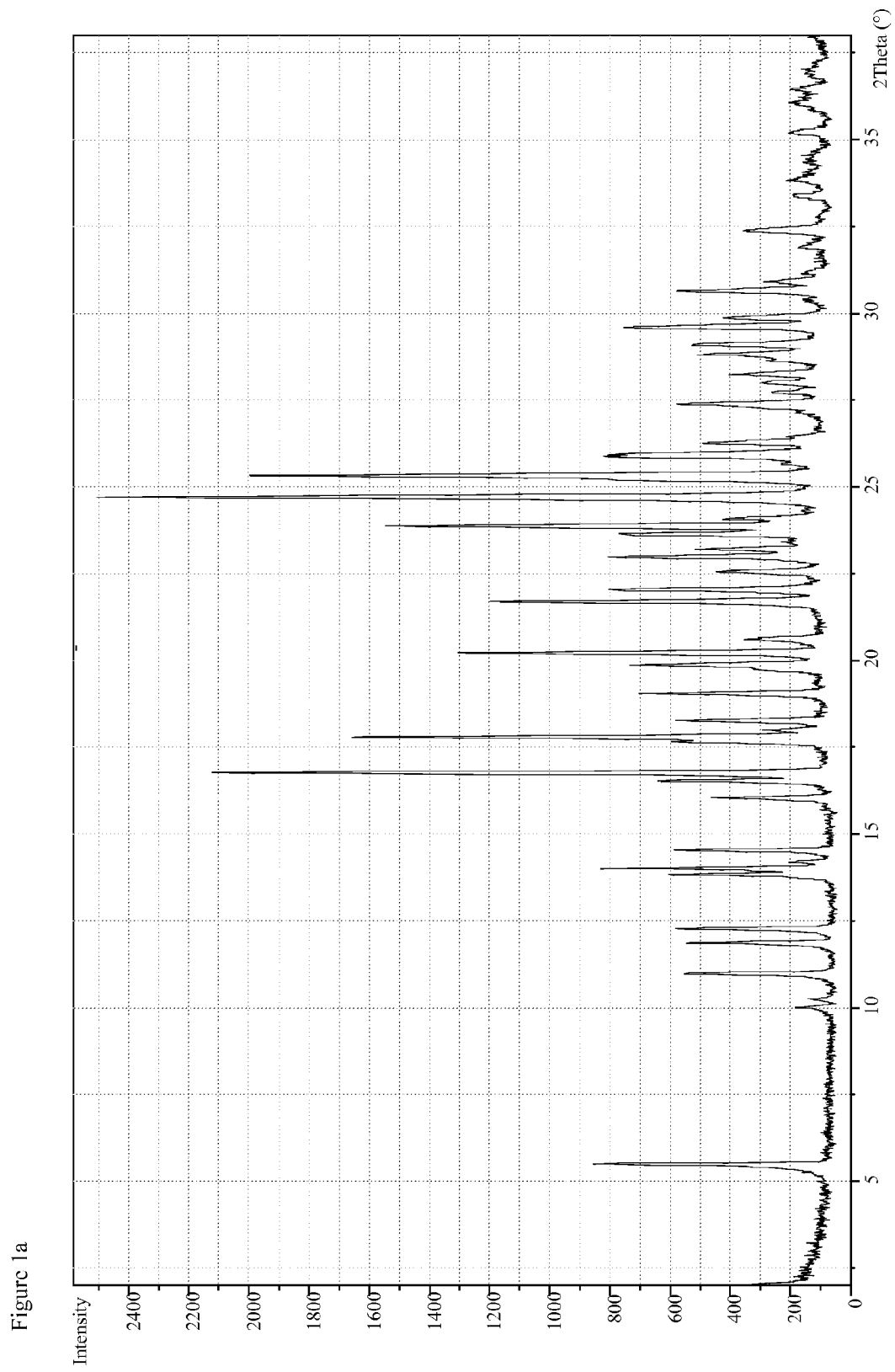
FIG. 1a: X-ray powder diffractogram of the novel solid form of 4-[[(6-chloropyridin-3-yl)methyl](2,2-difluoroethyl)amino]furan-2(5H)-one.
Figure 1B:
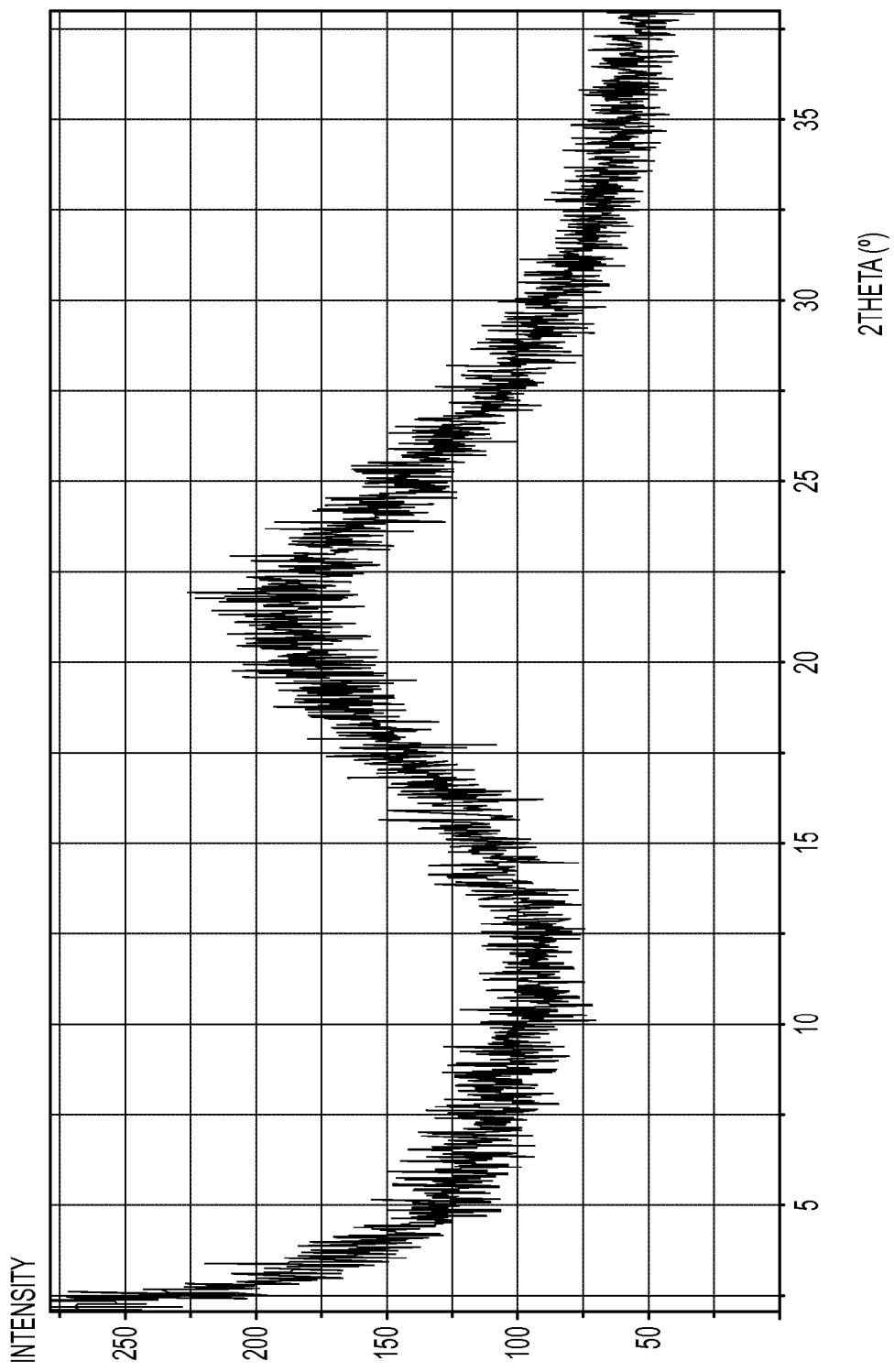
FIG. 1b: X-ray powder diffractogram of amorphous 4-[[(6-chloropyridin-3-yl)methyl](2,2-difluoroethyl)amino]furan-2(5H)-one prepared according to WO 2009/036899.
Figure 2A:
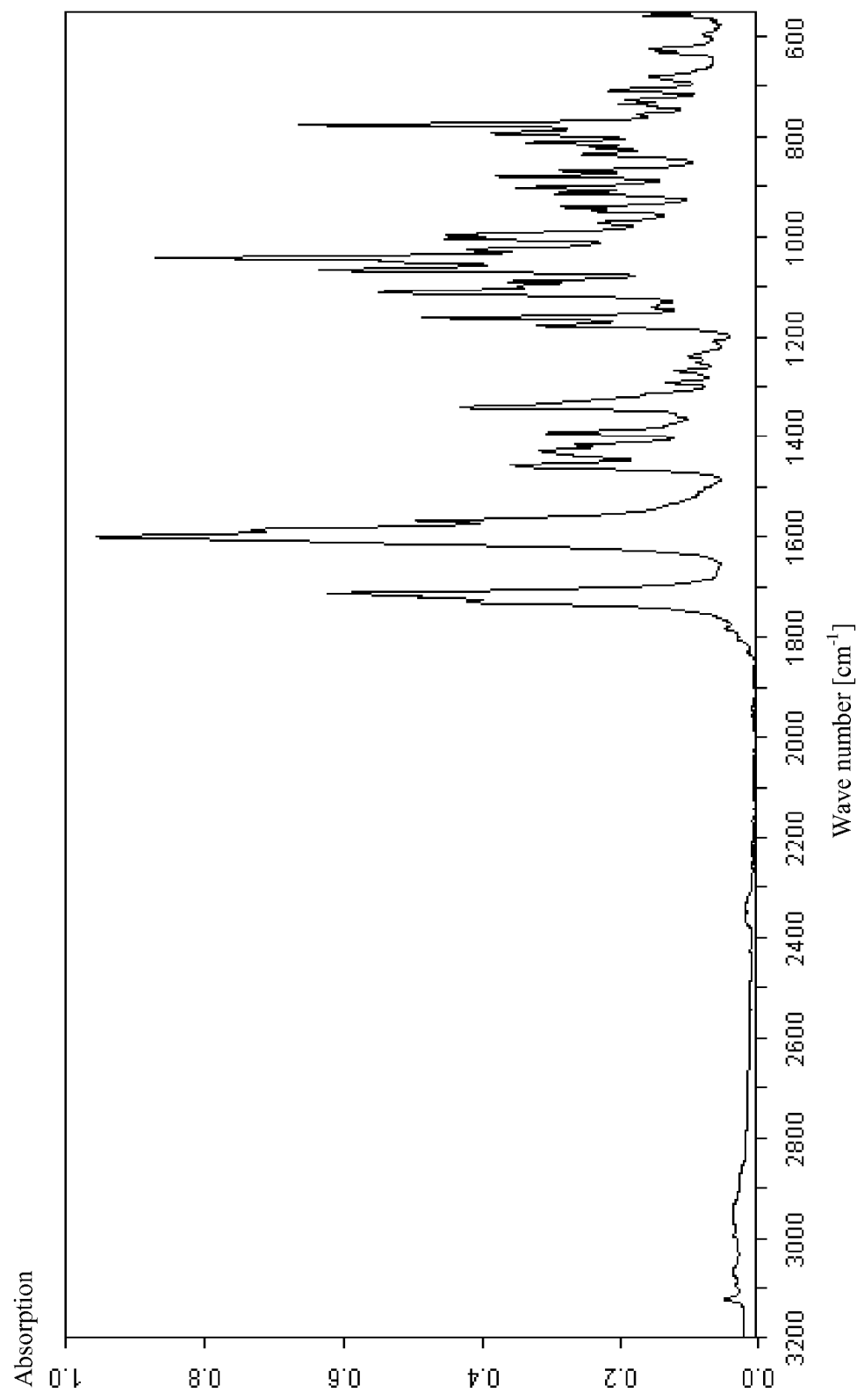
FIG. 2a: Infrared (IR) spectra of the novel solid form of 4-[[(6-chloropyridin-3-yl)methyl](2,2-difluoroethyl)amino]furan-2(5H)-one.
Figure 2B:
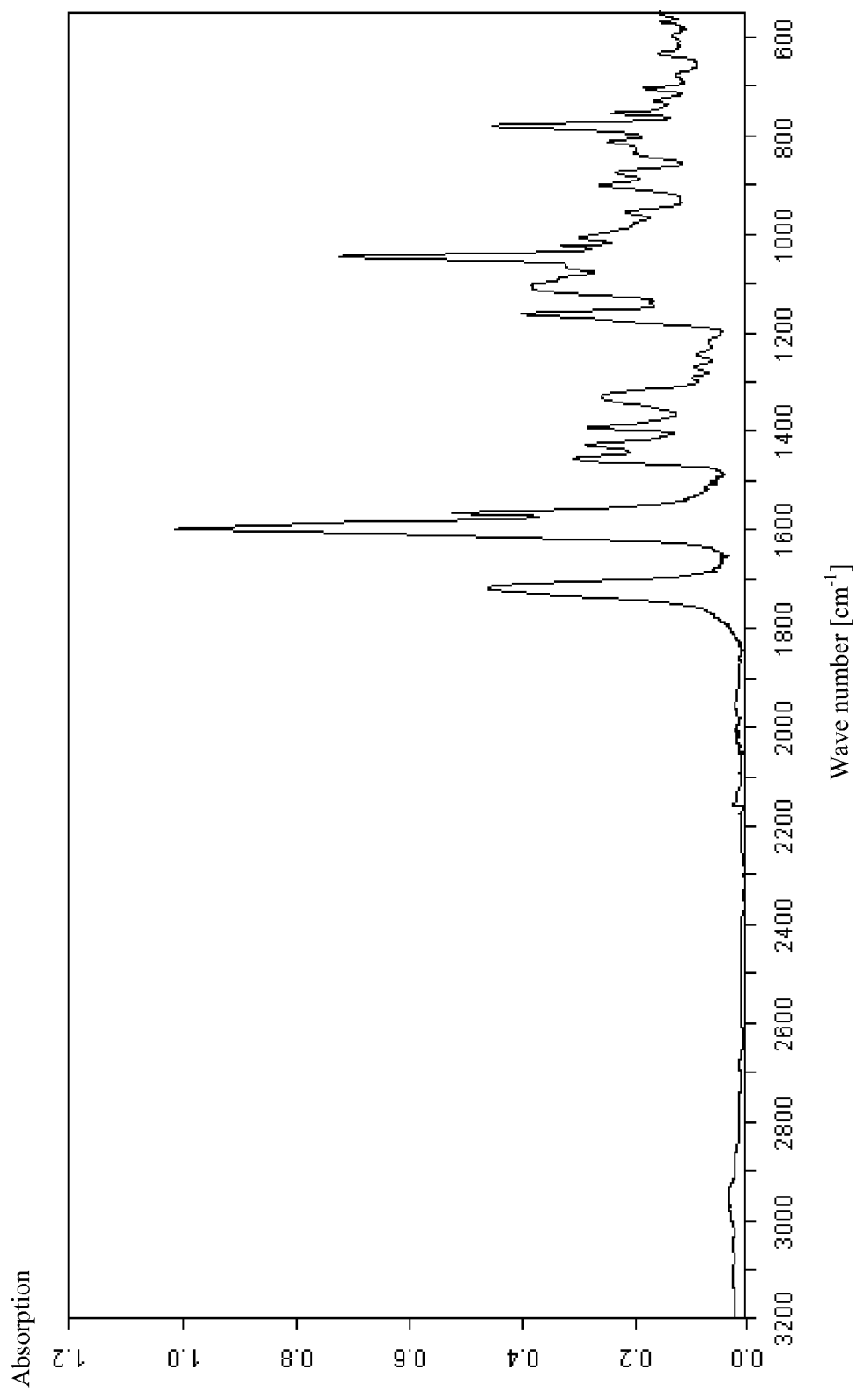
FIG. 2b: Infrared (IR) spectra of the amorphous form of 4-[[(6-chloropyridin-3-yl)methyl](2,2-difluoroethyl)amino]furan-2(5H)-one.
Figure 3A:
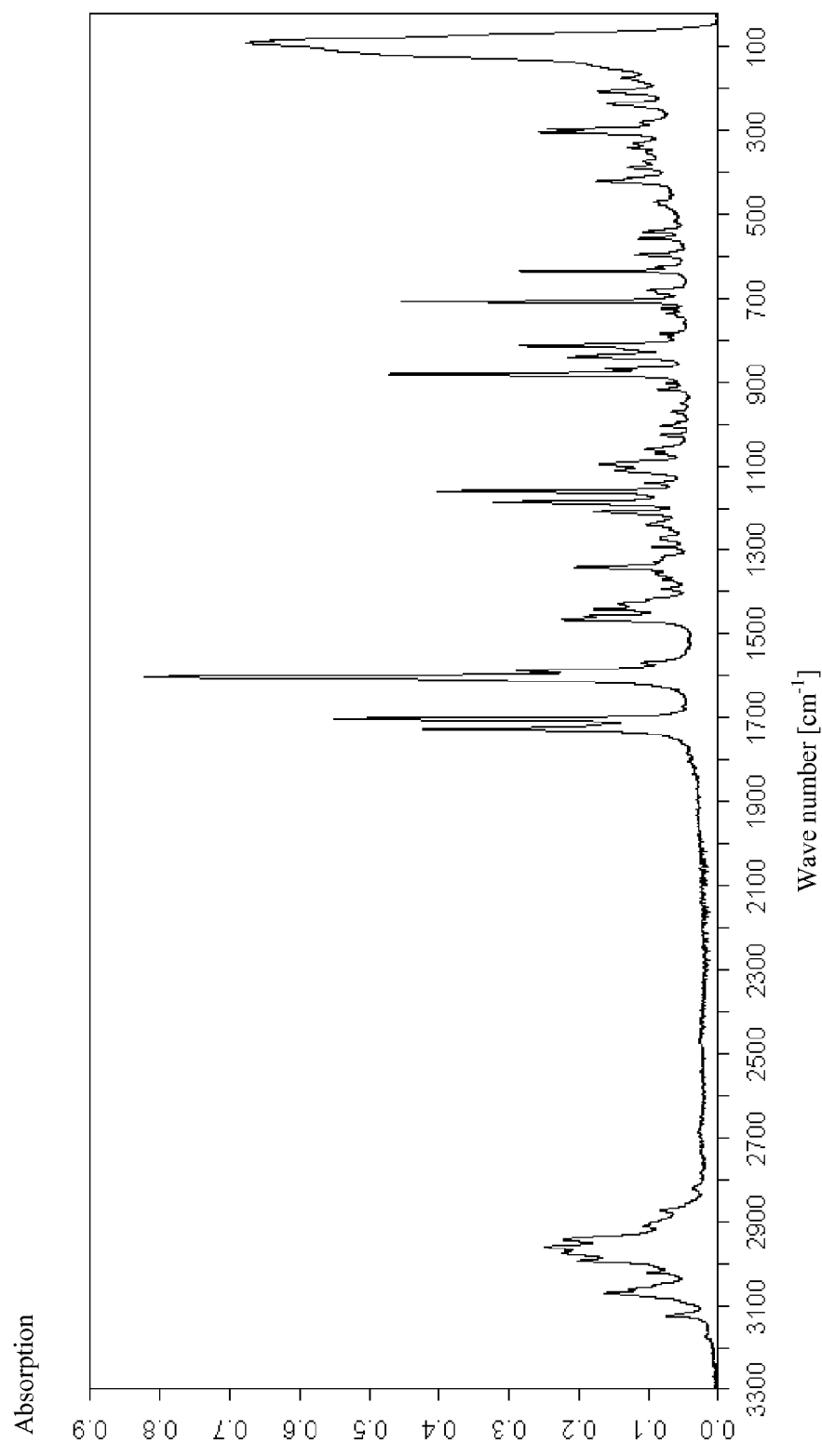
FIG. 3a: Raman spectra of the novel solid form of 4-[[(6-chloropyridin-3-yl)methyl](2,2-difluoroethyl)amino]furan-2(5H)-one.
Figure 3B:
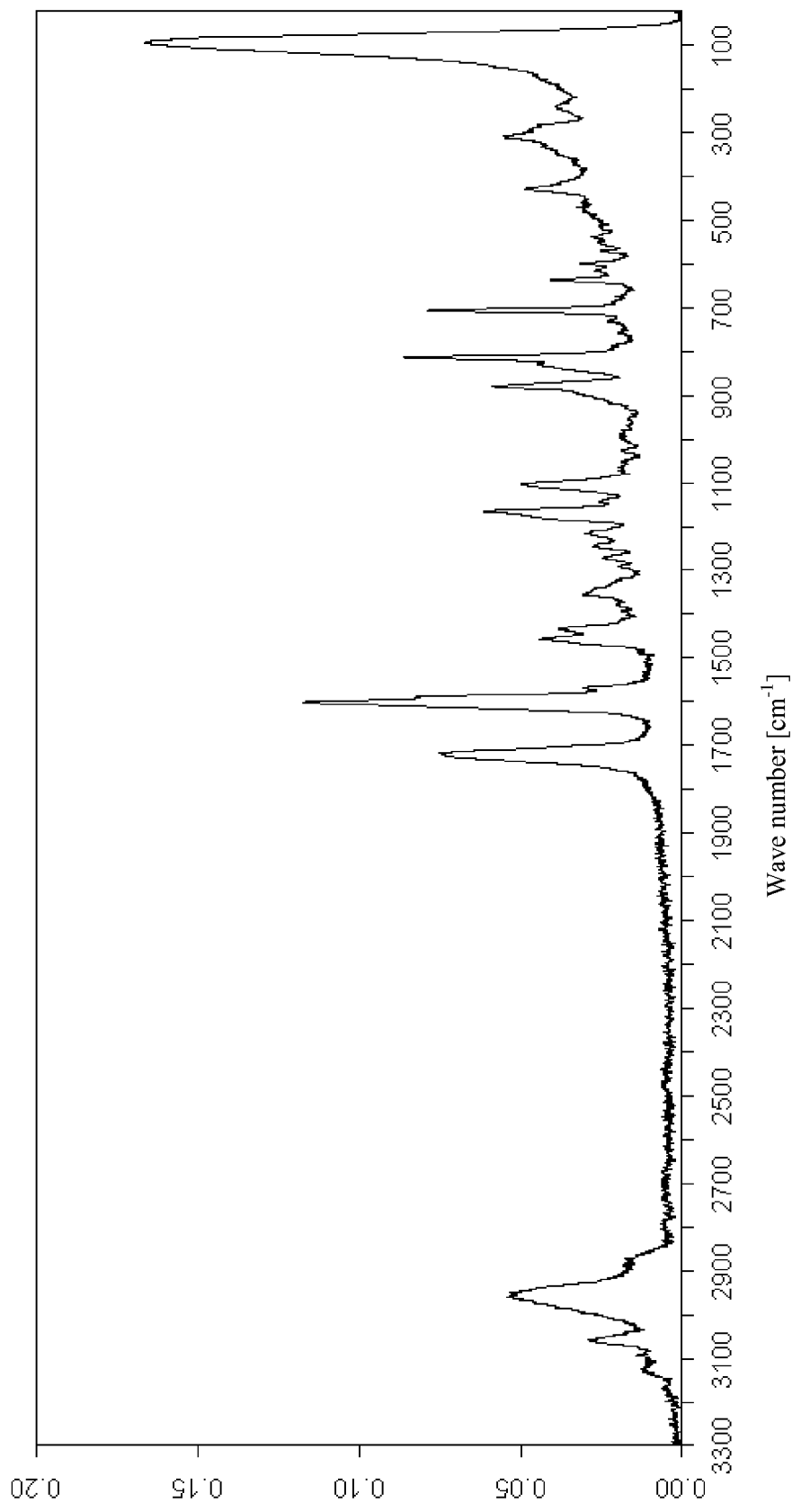
FIG. 3b: Raman spectra of the amorphous form of 4-[[(6-chloropyridin-3-yl)methyl](2,2-difluoroethyl)amino]furan-2(5H)-one.

According to a preferred embodiment of the present invention, the compound has a melting point in the range from 72° C. to 74° C. and the X-ray powder diffractogram of the novel solid form has the signals shown in FIG. 1a.

In addition to melting point and X-ray powder diffractogram, the novel solid form of 4-[[(6-chloropyridin-3-yl)methyl](2,2-difluoroethyl)amino]furan-2(5H)-one also has the main Raman bands shown in Table 2 and the main IR bands listed in Table 3. Tables 2 and 3 additionally each state the main bands of the amorphous form.

TABLE 2

Position of the main bands in the Raman spectrum of the known amorphous and the novel solid form known amorphous form [cm$^{-1}$]

3058 ± 1
2960 ± 1
1719 ± 1
1602 ± 1
1457 ± 1
1434 ± 1
1356 ± 1
1273 ± 1
1246 ± 1
1216 ± 1
1166 ± 1
1103 ± 1
880 ± 1
814 ± 1
707 ± 1
636 ± 1
599 ± 1
429 ± 1
308 ± 1
96 ± 1 novel solid form [cm$^{-1}$]

3126 ± 1
3072 ± 1
3022 ± 1
2994 ± 1
2974 ± 1
2960 ± 1
2944 ± 1
2911 ± 1
2874 ± 1
1727 ± 1
1702 ± 1
1602 ± 1
1588 ± 1
1568 ± 1
1467 ± 1
1441 ± 1
1429 ± 1
1392 ± 1
1342 ± 1
1293 ± 1
1276 ± 1
1240 ± 1
1209 ± 1
1187 ± 1
1160 ± 1
1140 ± 1
1112 ± 1
1096 ± 1
1060 ± 1
1026 ± 1
1005 ± 1
971 ± 1
917 ± 1
882 ± 1
869 ± 1
841 ± 1
813 ± 1
785 ± 1
725 ± 1
709 ± 1
682 ± 1
636 ± 1
597 ± 1
559 ± 1

TABLE 2-continued

Position of the main bands in the Raman spectrum of the known amorphous and the novel solid form 543 ± 1
471 ± 1
421 ± 1
389 ± 1
342 ± 1
305 ± 1
297 ± 1
237 ± 1
209 ± 1
176 ± 1
92 ± 1

TABLE 3

Position of the main bands of the infrared spectrum of the known amorphous form and the novel solid form known amorphous form [cm$^{-1}$]

3451 ± 2
1717 ± 2
1597 ± 2
1566 ± 2
1455 ± 2
1428 ± 2
1392 ± 2
1329 ± 2
1270 ± 2
1244 ± 2
1162 ± 2
1103 ± 2
1046 ± 2
1024 ± 2
1007 ± 2
955 ± 2
902 ± 2
876 ± 2
813 ± 2
781 ± 2
756 ± 2
729 ± 2
705 ± 2
633 ± 2
600 ± 2
569 ± 2 novel solid form [cm$^{-1}$]

3123 ± 2
1731 ± 2
1714 ± 2
1601 ± 2
1588 ± 2
1569 ± 2
1458 ± 2
1428 ± 2
1418 ± 2
1393 ± 2
1342 ± 2
1293 ± 2
1269 ± 2
1241 ± 2
1180 ± 2
1163 ± 2
1142 ± 2
1113 ± 2
1091 ± 2
1068 ± 2
1044 ± 2
1026 ± 2
1007 ± 2
1000 ± 2
974 ± 2
950 ± 2
943 ± 2

TABLE 3-continued

Position of the main bands of the infrared spectrum
of the known amorphous form and the novel solid form 915 ± 2
904 ± 2
882 ± 2
869 ± 2
837 ± 2
824 ± 2
814 ± 2
795 ± 2
779 ± 2
737 ± 2
729 ± 2
711 ± 2
682 ± 2
635 ± 2
627 ± 2
597 ± 2
560 ± 2

Surprisingly, it has been found that 4-[[(6-chloropyridin-3-yl)methyl](2,2-difluoroethyl)amino]furan-2(5H)-one in the novel solid form is sufficiently thermodynamically stable for economically relevant use and is not converted into another form even on prolonged storage.

This allows the preparation of suspension concentrates, oil-based suspension concentrates and, for example, water-dispersible granules and similar formulations for the treatment of seed.

By virtue of its stability, the compound 4-[[(6-chloropyridin-3-yl)methyl](2,2-difluoroethyl)amino]furan-2(5H)-one in the novel solid form is highly suitable for preparing compositions for controlling animal pests, in particular pests encountered in agriculture and forests. Accordingly, the invention also provides compositions for controlling such pests which comprise the novel solid form alone or as a mixture with auxiliaries and carriers, and also as a mixture with other active compounds.

The invention also encompasses compositions comprising the compound 4-[[(6-chloropyridin-3-yl)methyl](2,2-difluoroethyl)amino]furan-2(5H)-one in the novel solid form. Preference is given to compositions comprising less than 20% by weight of the novel solid form, particularly preferably less than 15% by weight, very particularly preferably less than 10% by weight, especially preferably less than 5% by weight and most preferably less than 4, 3, 2 or 1% by weight of the novel solid form. The term "composition" also comprises formulations and use forms.

The invention also provides processes for preparing compositions for controlling pests which make use of the compound 4-[[(6-chloropyridin-3-yl)methyl](2,2-difluoroethyl)amino]furan-2(5H)-one in the novel solid form. By using the compound 4-[[(6-chloropyridin-3-yl)methyl](2,2-difluoroethyl)amino]furan-2(5H)-one in the novel solid form, the safety of compositions comprising the compound 4-[[(6-chloropyridin-3-yl)methyl](2,2-difluoroethyl)amino]furan-2(5H)-one is increased, and the risk of incorrect dosages is thus reduced.

The compound 4-[[(6-chloropyridin-3-yl)methyl](2,2-difluoroethyl)amino]furan-2(5H)-one in the novel solid form can be converted in a known manner into the customary formulations, such as suspension concentrates, oil-based suspension concentrates, colloidal concentrates, dispersible concentrates, emulsifiable concentrates (emulsion concentrates), emulsion dressings, suspension dressings, granules, microgranules, suspoemulsions, water-soluble granules, water-soluble concentrates and water-dispersible granules, and also the corresponding ready-to-use formulations, using suitable auxiliaries and carriers or solvents. In this connection, the active compound should be present in a concentration of approximately 0.0001 to 90% by weight of the total mixture, i.e. in amounts which are sufficient in order to achieve the dosage level required. The formulations are prepared, for example, by extending the compound 4-[[(6-chloropyridin-3-yl)methyl](2,2-difluoroethyl)amino]furan-2(5H)-one in the novel solid form with water, solvents and/or carriers, using, if appropriate, emulsifiers and/or dispersants, and/or other auxiliaries, such as, for example, penetrants.

In the preparation of suspension concentrates including those used for the treatment of seed, in general further auxiliaries are added in addition to the active compound and an extender (water, solvent or oil). A wetting agent is used to moisten the active compound in the continuous phase, dispersants are used to stabilize the suspension in the liquid phase, emulsifiers are used to emulsify the non-aqueous phase of solvent- or oil-comprising suspension concentrates. If required, antifreeze agents, biocides, thickeners, colorants, spreading agents and/or penetrants are incorporated.

The novel solid compound 4-[[(6-chloropyridin-3-yl)methyl](2,2-difluoroethyl)amino]furan-2(5H)-one is obtained by the process described below. The compound 4-[[(6-chloropyridin-3-yl)methyl](2,2-difluoroethyl)amino]furan-2(5H)-one is prepared as described, for example, in WO 2007/115644 (page 51, Example 1). The 4-[[(6-chloropyridin-3-yl)methyl](2,2-difluoroethyl)amino]furan-2(5H)-one obtained in this manner is present in amorphous form.

To prepare the compound according to the invention, amorphous 4-[[(6-chloropyridin-3-yl)methyl](2,2-difluoroethyl)amino]furan-2(5H)-one is dissolved in a solvent or a solvent mixture at temperatures of at least 30° C., preferably at least 50° C., and slowly cooled until the desired crystals precipitate out. The amount of the solvent used is chosen such that the mixture remains readily stirrable during the crystallization.

The slow cooling takes place linearly or step-wise. Preferably, the cooling takes place step-wise, where the crystallization solution is stirred at a certain temperature, preferably at about 40° C., for a number of hours, preferably for 2 to 20 hours, particularly preferably for 4 to 20 hours, very particularly preferably for 4 to 16 hours, before it is cooled further until the desired crystals precipitate out.

If available, seed crystals may optionally be added to the solution to promote crystallization. In principle, addition of the seed crystals may be during stirring; however, in this case the solution has to be saturated to such a degree that the seed crystals do not go into solution. Preferably, the seed crystals are added after stirring.

Suitable solvents are all solvents in which 4-[[(6-chloropyridin-3-yl)methyl](2,2-difluoroethyl)amino]furan-2(5H)-one is soluble. Especially suitable are halogenated hydrocarbons (for example chlorobenzene, bromobenzene, dichlorobenzene, chlorotoluene, trichlorobenzene), ethers (for example ethyl propyl ether, methyl tert-butyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyl-THF and polyethers of ethylene oxide and/or propylene oxide), nitrated hydrocarbons (for example nitromethane, nitroethane, nitropropane, nitrobenzene, chloronitrobenzene, o-nitrotoluene), aliphatic, cycloaliphatic or aromatic hydrocarbons (for example pentane, n-hexane, n-heptane, n-octane, nonane, for example white spirits with components having boiling points in the range, for example, of from 40° C. to 250° C., cymene, petroleum fractions within a boiling range of from 70° C. to 190° C., cyclohexane, methylcyclohexane, petroleum ether, ligroin, octane, benzene, toluene, xylene), esters (for example malonates, acetic acid n-butyl ester (n-butyl acetate), methyl acetate, ethyl acetate, isobutyl acetate, dimethyl carbonate, diethyl carbonate, dibutyl carbonate, ethylene carbonate); and aliphatic alcohols (for example methanol, ethanol, n-propanol and isopropanol and n-butanol, tert-amyl alcohol). Preferred solvents are ethers, aromatic hydrocarbons such as benzene, toluene, xylene, chlorobenzene, esters and aliphatic alcohols and mixtures thereof. Particularly preferred solvents or solvent mixtures are isopropanol, toluene, methyl-THF, diethyl carbonate, chlorobenzene, n-butyl acetate and isobutyl acetate, n-butanol, ethanol, ethyl malonate, methyl t-butyl ether, and also mixtures of toluene and butanol, toluene and n-butyl acetate, ethyl malonate and methyl t-butyl ether, and butyl acetate and methyl t-butyl ether. Solvent mixtures of more than 2 components are also possible.

The compound 4-[[(6-chloropyridin-3-yl)methyl](2,2-difluoroethyl)amino]furan-2(5H)-one according to the invention in the novel solid form, in combination with good plant tolerance and favourable toxicity to warm-blooded animals and being tolerated well by the environment, is suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as crop protection agents. It is active against normally sensitive and resistant species and also against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus mactans, Metatetranychus* spp., *Nuphersa* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acalymma vittatum, Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnosterna consanguinea, Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Premnotrypes* spp., *Psylliodes* spp., *Ptinus* spp., *Rhizobius ventralis, Rhizopertha dominica, Sitophilus* spp., *Sphenophorus* spp., *Sternechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Diplopoda, for example, *Blaniulus guttulatus*.

From the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Ceratitis capitata, Chironomus* spp., *Chrysomyia* spp., *Cochliomyia* spp., *Contarinia* spp., *Cordylobia anthropophaga, Culex* spp., *Cuterebra* spp., *Dacus oleae, Dasyneura* spp., *Delia* spp., *Dermatobia hominis, Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia* spp., *Phorbia* spp., *Prodiplosis* spp., *Psila rosae, Rhagoletis* spp., *Stomoxys* spp., *Tabanus* spp., *Tannia* spp., *Tetanops* spp., *Tipula* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti*.

It is furthermore possible to control protozoa, such as *Eimeria*.

From the order of the Heteroptera, for example, *Anasa tristis, Antestiopsis* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahl-* bergella singularis, Scaptocoris castanea, Scotinophora spp., Stephanitis nashi, Tibraca spp., Triatoma spp.

From the order of the Homoptera, for example, *Acyrthosipon* spp., *Acrogonia* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus*, *Ferrisia* spp., *Geococcus coffeae*, *Hieroglyphus* spp., *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Sticocephala festina*, *Tenalaphara malayensis*, *Tinocallis caryaefoliae*, *Tomaspis* spp., *Toxoptera* spp., *Trialeurodes* spp., *Trioza* spp., *Typhlocyba* spp., *Unaspis* spp., *Viteus vitifolii*, *Zygina* spp.

From the order of the Hymenoptera, for example, *Athalia* spp., *Diprion* spp., *Hoplocampa* spp., *Lasius* spp., *Monomorium pharaonis*, *Vespa* spp.

From the order of the Isopoda, for example, *Armadillidium vulgare*, *Oniscus asellus* and *Porcellio scaber*.

From the order of the Isoptera, for example, *Acromyrmex* spp., *Atta* spp., *Cornitermes cumulans*, *Microtermes obesi*, *Odontotermes* spp., *Reticulitermes* spp.

From the order of the Lepidoptera, for example, *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Cheimatobia brumata*, *Chilo* spp., *Choristoneura* spp., *Clysia ambiguella*, *Cnaphalocerus* spp., *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia kuehniella*, *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocollectis* spp., *Lithophane antennata*, *Lobesia* spp., *Loxagrotis albicosta*, *Lymantria* spp., *Lyonetia* spp., *Malacosoma neustria*, *Maruca testulalis*, *Mamestra brassicae*, *Mocis* spp., *Mythimna separata*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phyllocnistis citrella*, *Phyllonorycter* spp., *Pieris* spp., *Platynota stultana*, *Plusia* spp., *Plutella xylostella*, *Prays* spp., *Prodenia* spp., *Protoparce* spp., *Pseudaletia* spp., *Pseudoplusia includens*, *Pyrausta nubilalis*, *Rachiplusia nu*, *Schoenobius* spp., *Scirpophaga* spp., *Scotia segetum*, *Sesamia* spp., *Sparganothis* spp., *Spodoptera* spp., *Stathmopoda* spp., *Stomopteryx subsecivella*, *Synanthedon* spp., *Tecia solanivora*, *Thermesia gemmatalis*, *Tinea pellionella*, *Tineola bisselliella*, *Tortrix* spp., *Trichoplusia* spp., *Tuta absoluta*, *Virachola* spp.

From the order of the Orthoptera, for example, *Acheta domesticus*, *Blatta orientalis*, *Blattella germanica*, *Dichroplus* spp., *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp. and *Xenopsylla cheopis*.

From the order of the Symphyla, for example, *Scutigerella* spp.

From the order of the Thysanoptera, for example, *Anaphothrips obscurus*, *Baliothrips biformis*, *Drepanothris reuteri*, *Enneothrips flavens*, *Frankliniella* spp., *Heliothrips* spp., *Hercinothrips femoralis*, *Rhipiphorothrips cruentatus*, *Scirtothrips* spp., *Taeniothrips cardamoni*, *Thrips* spp.

From the order of the Thysanura, for example, *Lepisma saccharina*.

The phytoparasitic nematodes include, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis*, *Trichodorus* spp., *Tylenchulus semipenetrans*, *Xiphinema* spp.

If appropriate, the compound according to the invention can, at certain concentrations or application rates, also be used as herbicide, safener, growth regulator or agent to improve plant properties, or as microbicide, for example as fungicide, antimycotic, bactericide, viricide (including agent against viroids) or as agent against MLO (Mycoplasma-like organisms) and RLO (*Rickettsia*-like organisms).

In addition to the formulations mentioned above, the compound 4-[[(6-chloropyridin-3-yl)methyl](2,2-difluoroethyl)amino]furan-2(5H)-one in the novel solid form can be converted into further formulations. Such formulations are, for example, solutions, emulsions, wettable powders, water- and oil-based suspensions, powders, dusts, pastes, soluble powders, soluble granules, granules for broadcasting, suspoemulsion concentrates, natural compounds impregnated with active compound, synthetic substances impregnated with active compound, fertilizers and also microencapsulations in polymeric substances. Preference according to the invention is given to solid formulations.

The formulations are produced in a known manner, for example by mixing the active compounds with extenders, that is, liquid solvents and/or solid carriers, optionally with the use of surfactants, that is to say wetting agents, emulsifiers, dispersants and/or antifoams. The formulations are prepared either in suitable facilities or else before or during application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as cyclohexanone), esters (including fats and oils) and (poly) ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics, such as xylene, toluene, or alkylnaphthalenes, aliphatic hydrocarbons or paraffins, for example mineral oil fractions, mineral and vegetable oils, alcohols and also their ethers and esters, ketones, such as methyl ethyl ketone, methyl isobutyl ketone or cyclohexanone, strongly polar solvents, such as N-methylpyrrolidone, dimethyl sulphoxide, and also water.

According to the invention, a carrier is a natural or synthetic, organic or inorganic substance which may be solid or liquid and with which the active compounds are mixed or bonded for better applicability, in particular for application to plants or plant parts or seed. The solid or liquid carrier is generally inert and should be suitable for use in agriculture.

Suitable solid or liquid carriers are:
for example ammonium salts and ground natural minerals such as kaolins, clays, talc, chalk, quartz, attapulgite, montmorillonite or diatomaceous earth, and ground synthetic materials such as highly disperse silica, alumina and silicates; suitable solid carriers for granules are: for example, crushed and fractionated natural rocks such as calcite, marble, sand, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the fatty alcohol-POE and/or POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. It is also possible to employ lignin and its sulphonic acid derivatives, unmodified and modified celluloses, aromatic and/or aliphatic sulphonic acids and also their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

Other possible additives are perfumes, mineral or vegetable oils which are optionally modified, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability, may also be present.

The active compound content of the use forms prepared from the formulations can vary within wide limits The active compound concentration of the use forms is in the range of from 0.00000001 to 97% by weight of active compound, preferably in the range of from 0.0000001 to 97% by weight, particularly preferably in the range of from 0.000001 to 83% by weight or 0.000001 to 5% by weight, and very particularly preferably in the range of from 0.0001 to 1% by weight.

The compound 4-[[(6-chloropyridin-3-yl)methyl](2,2-difluoroethyl)amino]furan-2(5H)-one in the novel solid form can be present in mixtures with other active compounds such as insecticides, attractants, sterilants, bactericides, acaricides, nematicides, fungicides, growth regulators, herbicides, safeners (for example cloquintocet-mexyl, fenchlorazole-ethyl, isoxadifen-ethyl, mefenpyr-diethyl, fenclorim and cumyluron), fertilizers or semiochemicals or else with agents for enhancing plant properties. This applies in particular to its commercial formulations and to the use forms prepared from these formulations. This applies both to active compound combinations and to tank mix mixtures.

Suitable mixing partners are in particular the following insecticides, acaricides and nematicides:
(1) acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion;
(2) GABA-gated chloride channel antagonists, such as, for example, organochlorines, for example chlordane and endosulfan (alpha-); or fiproles (phenylpyrazoles), for example ethiprole, fipronil, pyrafluprole and pyriprole;
(3) sodium channel modulators/voltage-dependent sodium channel blockers, such as, for example, pyrethroids, for example acrinathrin, allethrin (d-cis-trans, d-trans), bifenthrin, bioallethrin, bioallethrin-S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers], esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans-isomer], prallethrin, profluthrin, pyrethrins (pyrethrum), resmethrin, RU 15525, silafluofen, tefluthrin, tetramethrin [(1R)-isomers], tralomethrin, transfluthrin and ZXI 8901; or DDT; or methoxychlor;
(4) nicotinergic acetylcholine receptor agonists, such as, for example, neonicotinoids, for example acetamiprid, clothianidin, dinotefuran, imidacloprid, nitenpyram, thiacloprid, thiamethoxam; or nicotine;
(5) allosteric acetylcholine receptor modulators (agonists), such as, for example, spinosyns, for example spinetoram and spinosad;
(6) chloride channel activators, such as, for example, avermectins/milbemycins, for example abamectin, emamectin benzoate, lepimectin and milbemectin;
(7) juvenile hormone analogues, for example hydroprene, kinoprene, methoprene; or fenoxycarb; pyriproxyfen;
(8) active compounds with unknown or non-specific mechanisms of action, such as, for example, fumigants, for example methyl bromide and other alkyl halides; or chloropicrin; sulphuryl fluoride; borax; tartar emetic;
(9) selective antifeedants, for example pymetrozine; or flonicamid;
(10) mite growth inhibitors, for example clofentezine, diflovidazin, hexythiazox, etoxazole;
(11) microbial disruptors of the insect gut membrane, such as, for example, *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins, for example Cry1Ab, Cry1Ac, Cry1Fa, Cry2Ab, mCry3A, Cry3Ab, Cry3Bb, Cry34/35Ab1;
(12) oxidative phosphorylation inhibitors, ATP disruptors, such as, for example, diafenthiuron; or organotin compounds, for example azocyclotin, cyhexatin, fenbutatin oxide; or propargite; tetradifon;
(13) oxidative phoshorylation decouplers acting by interrupting the H proton gradient, such as, for example, chlorfenapyr and DNOC;
(14) nicotinergic acetylcholine receptor antagonists, such as, for example, bensultap, cartap (hydrochloride), thiocylam, and thiosultap (sodium);
(15) chitin biosynthesis inhibitors, type 0, such as, for example, benzoylureas, for example bistrifluron, chlorfluazuron, diflubenzuron, flucycloxuron, flufenoxuron, hexaflumuron, lufenuron, novaluron, novi-flumuron, teflubenzuron and triflumuron;
(16) chitin biosynthesis inhibitors, type 1, such as, for example, buprofezin;
(17) moulting disruptors, such as, for example, cyromazine;
(18) ecdysone agonists/disruptors, such as, for example, diacylhydrazines, for example chromafenozide, halofenozide, methoxyfenozide and tebufenozide;
(19) octopaminergic agonists, such as, for example, amitraz;
(20) complex-III electron transport inhibitors, such as, for example, hydramethylnone; acequinocyl; fluacrypyrim;
(21) complex-I electron transport inhibitors, for example from the group of the METI acaricides, for example fenazaquin, fenpyroximate, pyrimidifen, pyridaben, tebufenpyrad, tolfenpyrad; or rotenone (Derris);
(22) voltage-dependent sodium channel blockers, for example indoxacarb; metaflumizone;
(23) inhibitors of acetyl-CoA carboxylase, such as, for example, tetronic acid derivatives, for example spirodiclofen and spiromesifen; or tetramic acid derivatives, for example spirotetramat;
(24) complex-IV electron transport inhibitors, such as, for example, phosphines, for example aluminium phosphide, calcium phosphide, phosphine, zinc phosphide; or cyanide;
(25) complex-II electron transport inhibitors, such as, for example, cyenopyrafen; or
(28) ryanodine receptor effectors, such as, for example, diamides, for example, chlorantraniliprole (Rynaxypyr), cyantraniliprole (Cyazypyr) and flubendiamide.

Further active compounds with unknown mechanism of action, such as, for example, amidoflumet, benzoximate, bifenazate, chinomethionat, cryolite, cyflumetofen, dicofol, flufenerim, pyridalyl and pyrifluquinazon; or the known active compounds below: 4-{[(6-bromopyrid-3-yl)methyl] (2-fluoroethyl)amino}furan-2(5H)-one (known from WO 2007/115644), 4-{[(6-fluoropyrid-3-yl)methyl](2,2-difluoroethyl)amino}furan-2(5H)-one (known from WO 2007/115644), 4-{[(2-chloro-1,3-thiazol-5-yl)methyl](2-fluoroethyl)amino}furan-2(5H)-one (known from WO 2007/115644), 4-{[(6-chloropyrid-3-yl)methyl](2-fluoroethyl)amino}furan-2(5H)-one (known from WO 2007/115644), 4-{[(6-chloropyrid-3-yl)methyl](2,2-difluoroethyl)amino}furan-2(5H)-one (known from WO 2007/115644), 4-{[(6-chloro-5-fluoropyrid-3-yl)methyl](methyl)amino}furan-2(5H)-one (known from WO 2007/115643), 4-{[(5,6-dichloropyrid-3-yl)methyl](2-fluoroethyl)amino}furan-2(5H)-one (known from WO 2007/115646), 4-{[(6-chloro-5-fluoropyrid-3-yl)methyl](cyclopropyl)amino}furan-2(5H)-one (known from WO 2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), [(6-chloropyridin-3-yl)methyl](methyl)oxido-$\lambda^4$-sulphanylidenecyanamide (known from WO 2007/149134), [1-(6-chloropyridin-3-yl)ethyl](methyl)oxido-$\lambda^4$-sulphanylidenecyanamide (known from WO 2007/149134) and its diastereomers (A) and (B)

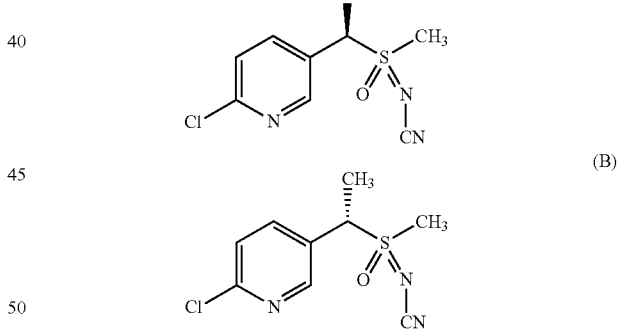

(also known from WO 2007/149134), [(6-trifluoromethylpyridin-3-yl)methyl](methyl)oxido-$\lambda^4$-sulphanylidenecyanamide (known from WO 2007/095229), sulfoxaflor (also known from WO 2007/149134), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911) and 1-{2,4-dimethyl-5-[(2,2,2-trifluoroethyl)sulphinyl]phenyl}-3-(trifluoromethyl)-1H-1,2,4-triazole (known from WO 1999/55668).

Suitable mixing components are furthermore the following fungicides:
(A) nucleic acid synthesis inhibitors, such as, for example, benalaxyl, benalaxyl-M, bupirimate, clozylacon, dimethirimol, ethirimol, furalaxyl, hymexazole, metalaxyl, metalaxyl-M, ofurace, oxadixyl and oxolinic acid;

(B) mitosis and cell division inhibitors, for example benomyl, carbendazim, chlorfenazole, diethofencarb, ethaboxam, fuberidazole, pencycuron, thiabendazole, thiophanate, thiophanate-methyl and zoxamide;

(C) respiration inhibitors (inhibitors of the respiratory chain), for example diflumetorim as inhibitor which acts on complex I of the respiratory chain; bixafen, boscalid, carboxin, fenfuram, flutolanil, fluopyram, furametpyr, furmecyclox, isopyrazam (mixture of the syn-epimeric racemate 1RS,4SR,9RS and the anti-epimeric racemate 1RS,4SR,9SR), isopyrazam (syn-epimeric racemate 1RS,4SR,9RS), isopyrazam (syn-epimeric enantiomer 1R,4S,9R), isopyrazam (syn-epimeric enantiomer 1S,4R,9S), isopyrazam (anti-epimeric racemate 1RS,4SR,9SR), isopyrazam (anti-epimeric enantiomer 1R,4S,9S), isopyrazam (anti-epimeric enantiomer 1S,4R,9R),
mepronil, oxycarboxin, penflufen, penthiopyrad, sedaxane, thifluzamid as inhibitors which act on complex II of the respiratory chain; amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyraoxystrobin, pyrametostrobin, pyribencarb, trifloxystrobin as inhibitors which act on complex III of the respiratory chain;

(D) decouplers, for example binapacryl, dinocap, fluazinam and meptyldinocap;

(E) ATP production inhibitors, for example fentin acetate, fentin chloride, fentin hydroxide and silthiofam;

(F) amino acid and protein biosynthesis inhibitors, for example andoprim, blasticidin-S, cyprodinil, kasugamycin, kasugamycin hydrochloride hydrate, mepanipyrim and pyrimethanil;

(G) signal transduction inhibitors, for example fenpiclonil, fludioxonil and quinoxyfen;

(H) lipid and membrane synthesis inhibitors, for example biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl and vinclozolin;

(I) ergosterol biosynthesis inhibitors, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulphate, imibenconazole, ipconazole, metconazole, myclobutanil, naftifine, nuarimol, oxpoconazole, paclobutrazole, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole and voriconazole;

(J) cell wall synthesis inhibitors, for example benthiavalicarb, dimethomorph, flumorph, iprovalicarb, mandipropamid, polyoxins, polyoxorim, prothiocarb, validamycin A and valefenalat;

(K) melanin biosynthesis inhibitors, for example carpropamid, diclocymet, fenoxanil, phthalide, pyroquilon and tricyclazole;

(L) resistance inductors, for example acibenzolar-S-methyl, probenazole and tiadinil;

(M) compounds with multi-site activity, for example Bordeaux mixture, captafol, captan, chlorothalonil, copper naphthenate, copper oxide, copper oxychloride, copper preparations such as, for example, copper hydroxide, copper sulphate, dichlofluanid, dithianon, dodine and its free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations such as, for example, calcium polysulphide, thiram, tolylfluanid, zineb and ziram;

(N) further compounds, for example 2,3-dibutyl-6-chlorothieno[2,3-d]pyrimidin-4(3H)-one, ethyl (2Z)-3-amino-2-cyano-3-phenylprop-2-enoate, 3-(difluoromethyl)-1-methyl-N-(3',4',5'-trifluorobiphenyl-2-yl)-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, (2E)-2-(2-{[6-(3-chloro-2-methylphenoxy)-5-fluoropyrimidin-4-yl]oxy}phenyl)-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, N-(3-ethyl-3,5,5-trimethylcyclohexyl)-3-(formylamino)-2-hydroxybenzamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (2E)-2-(methoxyimino)-N-methyl-2-(2-{[({(1E)-1-[3-(trifluoromethyl)phenyl]ethylidene}amino)oxy]-methyl}phenyl)ethanamide, (2E)-2-(methoxyimino)-N-methyl-2-{2-[(E)-({1-[3-(trifluoromethyl)-phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N-ethyl-N-methyl-N'-{2-methyl-5-(trifluoromethyl)-4-[3-(trimethylsilyl)propoxy]phenyl}imidoformamide, N-{5-(difluoromethyl)-2-methyl-4-[3-(trimethylsilyl)propoxy]phenyl}-N-ethyl-N-methylimidoformamide, O-{1-[(4-methoxyphenoxy)methyl]-2,2-dimethylpropyl}1H-imidazole-1-carbothioate, N-[2-(4-{[3-(4-chlorophenyl)prop-2-yn-1-yl]oxy}-3-methoxyphenyl)ethyl]-$N^2$-(methylsulphonyl)valinamide, 5-chloro-7-(4-methylpiperidin-1-yl)-6-(2,4,6-trifluorophenyl)[1,2,4]triazolo[1,5-a]pyrimidine, 5-amino-1,3,4-thiadiazole-2-thiol, propamocarb-fosetyl, 1-[(4-methoxyphenoxy)methyl]-2,2-dimethylpropyl 1H-imidazole-1-carboxylate, 1-methyl-N-[2-(1,1,2,2-tetrafluoroethoxy)phenyl]-3-(trifluoromethyl)-1H-pyrazole-4-carboxamide, 2,3,5,6-tetrachloro-4-(methylsulphonyl)pyridine, 2-butoxy-6-iodo-3-propyl-4H-chromen-4-one, 2-phenylphenol and its salts, 3-(difluoromethyl)-1-methyl-N-[2-(1,1,2,2-tetrafluoroethoxy)phenyl]-1H-pyrazole-4-carboxamide, 3,4,5-trichloropyridine-2,6-dicarbonitrile, 3-[5-(4-chlorophenyl)-2,3-dimethylisoxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 8-hydroxyquinoline, 8-hydroxyquinoline sulphate, tebufloquin, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, ametoctradin, benthiazol, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, bethoxazin, capsimycin, carvone, chinomethionat, chloroneb, cufraneb, cyflufenamid, cymoxanil, cyprosulfamide, dazomet, debacarb, dichlorophen, diclomezine, dicloran, difenzoquat, difenzoquat methylsulphate, diphenylamine, ecomat, ferimzone, flumetover, fluopicolide, fluoromide, flusulfamide, flutianil, fosetyl-aluminium, fosetyl-calcium, fosetyl-sodium, hexachlorobenzene, irumamycin, isotianil, methasulfocarb, methyl(2E)-2-{2-[({cyclopropyl[(4-methoxyphenyl)imino]methyl}thio)methyl]phenyl}-3-methoxyacrylate, methyl isothiocyanate, metrafenone, (5-chloro-2-methoxy-4-methylpyridin-3-yl)(2,3,4-trimethoxy-6-methylphenyl)methanone, mildiomycin, tolnifanide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(Z)-[(cyclopropylmethoxy)imino][6-(difluoromethoxy)-2,3-difluorophenyl]methyl}-2-phenylacetamide, N-{(E)-[(cyclopropylmethoxy)imino][6-(difluoromethoxy)-2,3-difluorophenyl]methyl}-2-phenylacetamide, natamycin, nickel dimethyldithiocarbamate, nitrothal-isopropyl, octhilinone, oxamocarb, oxyfenthiin, pentachlorophenol and its salts, phenazine-1-carboxylic acid, phenothrin, phosphoric acid and its salts, propamocarb fosetylate, propanosine-sodium, proquinazid, pyrrolnitrin, quintozene, S-prop-2-en-1-yl 5-amino-2-(1-methylethyl)-4-(2-methylphenyl)-3-oxo-2,3-dihydro-1H-pyrazole-1-carbothioate, tecloftalam, tecnazene, triazoxide, trichlamide, 5-chloro-N-phenyl-N'-prop-2-yn-1-ylthiophene-2-sulphonohydrazide, zarilamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, and pentyl{6-[({[(1-methyl-1H-tetrazol-5-yl)(phenyl)methylidene]amino}oxy)methyl]pyridin-2-yl}carbamate.

Suitable mixing components also include the following herbicides and plant growth regulators: acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidochlor, amidosulfuron, aminopyralid, amitrole, ammonium sulphamate, ancymidol, anilofos, asulam, atrazine, azafenidin, azimsulfuron, aziprotryn, BAH-043, BAS-140H, BAS-693H, BAS-714H, BAS-762H, BAS-776H, BAS-800H, beflubutamid, benazolin, benazolin-ethyl, bencarbazone, benfluralin, benfuresate, bensulide, bensulfuron-methyl, bentazone, benzfendizone, benzobicyclon, benzofenap, benzofluor, benzoylprop, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat dibromide, dithiopyr, diuron, DNOC, eglinazine-ethyl, endothal, EPTC, esprocarb, ethalfluralin, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulphonamide, fenoprop, fenoxaprop, fenoxaprop-P, fenoxaprop-ethyl, fenoxaprop-P-ethyl, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, L-glufosinate, L-glufosinate-ammonium, glufosinate-ammonium, glyphosate, glyphosate-isopropylammonium, H-9201, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HNPC-9908, HOK-201, HW-02, imazamethabenz, imazamethabenz-methyl, imazamox, imazapic, imazapyr, imazaquin, imazethapyr, imazosulfuron, inabenfide, indanofan, indoleacetic acid (IAA), 4-indol-3-ylbutyric acid (IBA), iodosulfuron, iodosulfuron-methyl-sodium, ioxynil, isocarbamid, isopropalin, isoproturon, isouron, isoxaben, isoxachlortole, isoxaflutole, isoxapyrifop, IDH-100, KUH-043, KUH-071, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat chloride, mesosulfuron, mesosulfuron-methyl, mesotrione, methabenzthiazuron, metam, metamifop, metamitron, metazachlor, methazole, methoxyphenone, methyldymron, 1-methylcyclopropene, methyl isothiocyanate, metobenzuron, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulphate, monolinuron, monosulfuron, monuron, MT 128, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron-ethyl, pyrazoxyfen, pyribambenz, pyribambenz-isopropyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, secbumeton, sethoxydim, siduron, simazine, simetryn, SN-106279, sulcotrione, sulfallate (CDEC), sulfentrazone, sulfometuron, sulfometuron-methyl, sulfosate (glyphosate-trimesium), sulfosulfuron, SYN-523, SYP-249, SYP-298, SYP-300, tebutam, tebuthiuron, tecnazene, tefuryltrione, tembotrione, tepraloxydim, terbacil, terbucarb, terbuchlor, terbumeton, terbuthylazine, terbutryn, TH-547, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0166, ZJ-0270, ZJ-0543, or ZJ-0862 and also the following compounds

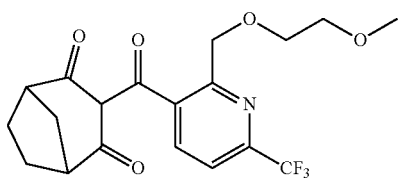

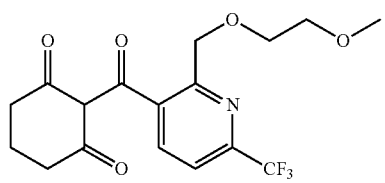

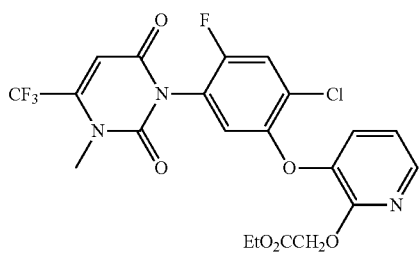

-continued

Here, the active compounds are referred to either by the "common name" in accordance with the International Organization for Standardization (ISO) or by their chemical name or code number, and in each case include all use forms, such as acids, salts, esters or modifications, such as isomers, stereoisomers and optical isomers. One or else more use forms or modifications are mentioned by way of example.

The invention also relates to compositions for controlling animal pests, in particular pests encountered in agriculture and in forests, which compositions comprise the novel solid form of 4-[[(6-chloropyridin-3-yl)methyl](2,2-difluoroethyl)amino]furan-2(5H)-one and at least one of the active compounds mentioned above.

When used as insecticide, the compound 4-[[(6-chloropyridin-3-yl)methyl](2,2-difluoroethyl)amino]-furan-2(5H)-one in the novel solid form can be present in its commercial formulations and in the use forms, prepared from these formulations, as a mixture with synergists. Synergists are compounds which increase the action of the active compounds, without it being necessary for the synergist added to be active itself.

When used as insecticides, the compound 4-[[(6-chloropyridin-3-yl)methyl](2,2-difluoroethyl)amino]-furan-2(5H)-one in the novel solid form can likewise be present in its commercial formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits The active compound concentration of the use forms can be from 0.00000001 to 95% by weight of active compound, preferably between 0.00001 and 1% by weight.

All plants and plant parts can be treated in accordance with the invention. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and also vegetative and generative propagation material, for example cuttings, tubers, rhizomes, slips and seed.

Treatment according to the invention of the plants and plant parts with the novel solid active compound or the active compound combinations comprising the novel solid active compound is carried out directly or by allowing the compounds to act on the surroundings, environment or storage space by the customary treatment methods, for example by immersion, spraying, evaporation, fogging, scattering, painting on, injection and, in the case of propagation material, in particular in the case of seeds, also by applying one or more coats.

The following plants may be mentioned as plants which can be treated according to the invention: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana plants and banana plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leeks, onions), *Papilionaceae* sp. (for example peas); major crop plants such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflowers, brussels sprouts, pak choi, kohlrabi, garden radish, and also oilseed rape, mustard, horseradish and cress), *Fabacae* sp. (for example beans, peanuts), *Papilionaceae* sp. (for example soya beans), *Solanaceae* sp. (for example potatoes), *Chenopodiaceae* sp. (for example sugar beet, fodder beet, Swiss chard, beetroot); useful plants and ornamental plants in gardens and forests; and in each case genetically modified types of these plants.

Treatment according to the invention of the plants and plant parts with the novel solid active compound or the active compound combinations according to the invention is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

Most of the damage to crop plants which is caused by pests occurs as early as when the seed is infested during storage and after the seed is introduced into the soil, and during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The present invention therefore in particular also relates to a method for the protection of seed and germinating plants, from attack by pests, by treating the seed with a composition according to the invention. The invention likewise relates to the use of the compositions according to the invention for the treatment of seed for protecting the seed and the resulting plant from pests. Furthermore, the invention relates to seed which has been treated with a composition according to the invention so as to afford protection from pests. Seed is understood as meaning conventional seed or transgenic seed.

In the case of transgenic seed, the plants originating from this seed are capable of expressing a protein directed against pests. This takes the form of seed of plants which, as a rule, comprise at least one heterologous gene which governs the expression of a polypeptide with in particular insecticidal properties. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. and whose gene product shows activity against the European corn borer and/or the corn root worm. It is particularly preferably a heterologous gene derived from *Bacillus thuringiensis*.

By treating such seed with the compositions according to the invention, certain pests can be controlled merely by the expression of the, for example, insecticidal protein, and additionally damage to the seed may be averted by the compositions according to the invention.

The compositions according to the invention are suitable for protecting seed of any plant variety as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, millet, wheat, barley, oats, rye, sunflower, tobacco, potatoes or vegetables (for example tomatoes, cabbage species). The compositions according to the invention are likewise suitable for treating the seed of fruit plants and vegetables as already mentioned above. The treatment of the seed of maize, soya beans, cotton, wheat and canola or oilseed rape is of particular importance.

Within the context of the present invention, the composition according to the invention is applied to the seed either alone or in a suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which can have phytotoxic effects at certain application rates.

The compositions according to the invention can be applied directly, i.e. without containing any other components and undiluted. In general, it is preferred to apply the compositions to the seed in the form of a suitable formulation. Suitable formulations and methods for treating seed are known to the person skilled in the art and are described, for example, in the following documents: U.S. Pat. No. 4,272, 417 A, U.S. Pat. No. 4,245,432 A, U.S. Pat. No. 4,808,430 A, U.S. Pat. No. 5,876,739 A, US 2003/0176428 A1, WO 2002/ 080675 A1, WO 2002/028186 A2.

The novel solid form of 4-[[(6-chloropyridin-3-yl)methyl] (2,2-difluoroethyl)amino]furan-2(5H)-one can be converted into the customary seed dressing formulations, such as solutions, emulsions, suspensions, powders, foams, slurries or other coating materials for seed, and also ULV formulations. These formulations are prepared in a known manner, by mixing the active compounds with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. In this context, not only pigments, which are sparingly soluble in water, but also dyes, which are soluble in water, may be used. Examples which may be mentioned are the colorants known by the names Rhodamin B, C.I. Pigment Red 112 and C.I. Solvent Red 1.

Suitable wetting agents which may be present in the seed-dressing formulations which can be used in accordance with the invention are all substances which promote wetting and which are conventionally used for the formulation of agrochemical active compounds. Preference is given to using alkylnaphthalenesulphonates, such as diisopropyl- or diisobutylnaphthalenesulphonates.

Suitable dispersants and/or emulsifiers which may be present in the seed-dressing formulations which can be used in accordance with the invention are all nonionic, anionic and cationic dispersants conventionally used for the formulation of agrochemical active compounds. Preference is given to using nonionic or anionic dispersants or mixtures of nonionic or anionic dispersants. Suitable nonionic dispersants which may be mentioned are, in particular, ethylene oxide/propylene oxide block polymers, alkylphenol polyglycol ethers and tristryrylphenol polyglycol ether, and their phosphated or sulphated derivatives. Suitable anionic dispersants are, in particular, lignosulphonates, polyacrylic acid salts and arylsulphonate/formaldehyde condensates.

Antifoams which may be present in the seed-dressing formulations which can be used in accordance with the invention are all foam-inhibiting substances conventionally used for the formulation of agrochemical active compounds. Silicone antifoams and magnesium stearate can preferably be used.

Preservatives which may be present in the seed-dressing formulations which can be used in accordance with the invention are all substances which can be employed for such purposes in agrochemical compositions. Dichlorophene and benzyl alcohol hemiformal may be mentioned by way of example.

Secondary thickeners which may be present in the seed-dressing formulations which can be used in accordance with the invention are all substances which can be employed for such purposes in agrochemical compositions. Cellulose derivatives, acrylic acid derivatives, xanthan, modified clays and finely divided silica are preferred.

Adhesives which may be present in the seed-dressing formulations which can be used in accordance with the invention are all customary binders which can be employed in seed-dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schädlingsbekämpfungsmittel" [Chemistry of crop protection agents and pesticides], vol. 2, Springer Verlag, 1970, p. 401-412).

The seed-dressing formulations which can be used in accordance with the invention can be employed for the treatment of a wide range of seed, including the seed of transgenic plants, either directly or after previously having been diluted with water. In this context, additional synergistic effects may also occur in cooperation with the substances formed by expression.

All mixers which can conventionally be employed for the seed-dressing operation are suitable for treating seed with the seed-dressing formulations which can be used in accordance with the invention or with the preparations prepared therefrom by addition of water. Specifically, a procedure is followed during the seed-dressing operation in which the seed is placed into a mixer, the specific desired amount of seed-dressing formulations, either as such or after previously having been diluted with water, is added, and everything is mixed until the formulation is distributed uniformly on the seed. If appropriate, this is followed by a drying process.

As already mentioned above, it is possible to treat all plants and their parts according to the invention. In a preferred embodiment, wild plant species and plant cultivars, or those obtained by conventional biological breeding, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, biotypes or genotypes.

Depending on the plant species or plant cultivars, their location and growth conditions (soils, climate, vegetation period, nutrition), the treatment according to the invention may also result in superadditive ("synergistic") effects. Thus possible are, for example, reduced application rates and/or a widening of the activity spectrum and/or an increase of the activity of the compounds and compositions usable according to the invention, better plant growth, increased tolerance to high or low temperatures, increased tolerance to drought or to water or soil salt content, increased flowering, easier harvesting, accelerated maturation, higher harvest yields, higher quality and/or higher nutritional value of the harvested products, increased storability and/or processability of the harvested products, which exceed the effects normally to be expected.

The preferred transgenic plants or plant cultivars (i.e. those obtained by genetic engineering) which are to be treated according to the invention include all plants which, in the genetic modification, received genetic material which imparts particularly advantageous useful properties ("traits") to these plants. Examples of such properties are better plant growth, increased tolerance to high or low temperatures, increased tolerance to drought or to water or soil salt content, increased flowering, easier harvesting, accelerated maturation, higher harvest yields, higher quality and/or a higher nutritional value of the harvested products, better storability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other types of vegetable, cotton, tobacco, oilseed rape and also fruit plants (with the fruits apples, pears, citrus fruits and grapes), with particular emphasis being given to maize, soya beans, potatoes, cotton, tobacco and oilseed rape. Traits that are emphasized in particular are increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defence of the plants against fungi, bacteria and viruses by systemic acquired resistance (SAR), systemin, phytoalexins, elicitors and also resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinothricin (for example the "PAT" gene). The genes which impart the desired traits in question can also be present in combinations with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance against glyphosate, for example maize, cotton, soya beans), Liberty Link® (tolerance against phosphinothricin, for example oilseed rape), IMI® (tolerance against imidazolinones) and STS® (tolerance against sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The novel solid form of 4-[[(6-chloropyridin-3-yl)methyl] (2,2-difluoroethyl)amino]furan-2(5H)-one can also be employed in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattella germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The novel solid form of 4-[[(6-chloropyridin-3-yl)methyl] (2,2-difluoroethyl)amino]furan-2(5H)-one is also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The novel solid form of 4-[[(6-chloropyridin-3-yl)methyl] (2,2-difluoroethyl)amino]furan-2(5H)-one is used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

In the use according to the invention in animal husbandry, for example in the management of cattle, poultry, pets, the active compounds or compositions can be used as suitable formulations, for example powders, emulsions, free-flowing compositions. Usually, suitable formulations comprise the active compounds in a concentration in the range from 0.1 to 80% by weight, preferably in the range from 1 to 60% by weight, particularly preferably in the range from 5 to 30% by weight. The formulations can be applied directly or in diluted form, preferably after 100- to 10 000-fold dilution. The active compounds and the compositions can also be used as a chemical bath.

Moreover, it has been found that the novel solid form of 4-[[(6-chloropyridin-3-yl)methyl](2,2-difluoroethyl)amino] furan-2(5H)-one and the compositions according to the invention can also be used in the protection of materials.

The following insects may be mentioned as examples and as preferred—but without a limitation:

beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;* dermapterans, such as *Sirex juvencus, Urocerus gigas, Urocerus gigas taignus, Urocerus augur;* termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;* bristletails, such as *Lepisma saccarina.*

Industrial materials in the present connection are to be understood as meaning non-living materials, such as, preferably, plastics, adhesives, sizes, papers and cards, leather, wood and processed wood products and coating compositions.

The novel solid form of 4-[[(6-chloropyridin-3-yl)methyl] (2,2-difluoroethyl)amino]furan-2(5H)-one can also be employed for protecting objects which come into contact with saltwater or brackish water, in particular hulls, screens, nets, buildings, docks and quays and signalling systems, against fouling.

Furthermore, the compounds according to the invention can be used alone or in combinations with other active compounds as antifouling compositions.

The novel solid form of 4-[[(6-chloropyridin-3-yl)methyl] (2,2-difluoroethyl)amino]furan-2(5H)-one is also suitable for controlling animal pests in the domestic field, in hygiene and in the protection of stored products, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric acid esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

The figures and examples below illustrate the invention without limiting it. The solvent systems used in the examples below are particularly preferred.

X-ray powder diffractometry spectra were recorded on an XPERT-PRO diffractometer using Cu—Kα radiation (wavelength 1.54060 Å) at 25° C., where the 2Θ value can be in the range of 2-38°. The spectrum was recorded using a step width of 0.0130 °2Θ.

Infrared (IR) spectra were recorded on a Bruker Tensor 37 FT-IR spectrometer comprising a Diamond ATR Unit from Specac over a wavelength range of 550-4000 $cm^{-1}$. The resolution of the instrument is 2 $cm^{-1}$. 64 scans were carried out per spectrum.

Raman spectra were recorded on a Bruker RFS/100 FT-Raman spectrometer whose laser has a laser wave number of 15798.7 cm$^{-1}$. The resolution of the instrument is 1 cm$^{-1}$. 128 scans were carried out per spectrum.

A): Preparation of 4-[[(6-chloropyridin-3-yl)methyl] (2,2-difluoroethyl)amino]furan-2(5H)-one According to WO 2009/036899 (Amorphous)

At room temperature, 11.5 g of potassium bisulphate are added to a suspension of 10.4 g of 4-(ethoxycarbonyl)-5-oxo-2,5-dihydrofuran-3-olate potassium salt and 7.5 g of N-[(6-chloropyridin-3-yl)methyl)-2,2-difluoroethylamine in 68 ml of butyronitrile. The mixture is stirred at a temperature of from 90 to 95° C. for 3 hours. The mixture is then cooled to room temperature, 120 ml of water and 120 ml of dichloromethane are added, the organic phase is separated off and the aqueous phase is extracted twice with in each case 120 ml of methylene chloride. The combined organic phases are concentrated to dryness. This gives 11.4 g of amorphous 4-[[(6-chloropyridin-3-yl)methyl](2,2-difluoroethyl)amino]furan-2(5H)-one in a purity of 84% (this corresponds to a yield of 92%).

$^1$H-NMR (CDCl$_3$, 298K) δ: 3.53 (td, 2H), 4.52 (s, 2H), 4.82 (s, 2H), 4.83 (s, 1H), 5.96 (tt, 1H), 7.37 (d, 1H), 7.55 (dd, 1H), 8.27 (d, 1H)

B): Preparation of the Novel Solid Form

Preparation Example 1

27 ml of methyl tert-butyl ether and 3 ml of n-butyl acetate are added to 20 g of the amorphous 4-[[(6-chloropyridin-3-yl)methyl](2,2-difluoroethyl)amino]furan-2(5H)-one, and the mixture is heated to 60° C. The mixture is then cooled at 0.5° C./min to 40° C. and stirred at 40° C. for 8 h. The mixture is then cooled to 35° C. over a period of 1 h and then cooled to 25° C. The precipitated crystals are filtered off with suction and washed with 5 ml of methyl tert-butyl ether. The crystals are dried at temperatures of less than 40° C. under reduced pressure. This gives 19 g of crystalline 4-[[(6-chloropyridin-3-yl)methyl](2,2-difluoroethyl)amino]furan-2(5H)-one having a melting point in the range of 72-74° C.

The $^1$H-NMR (CDCl$_3$, 298K) corresponds to that of amorphous 4-[[(6-chloropyridin-3-yl)methyl](2,2-difluoroethyl) amino]furan-2(5H)-one as indicated above.

Preparation Example 2

22.5 ml of toluene and 7.5 ml of n-butyl acetate are added to 20 g of the amorphous 44-[[(6-chloropyridin-3-yl)methyl] (2,2-difluoroethyl)amino]furan-2(5H)-one, and the mixture is heated to 60° C. The mixture is then cooled at 0.5° C./min to 40° C. and stirred at 40° C. for 8 h. The mixture is then cooled to 35° C. over a period of 1 h and then cooled to 25° C. The precipitated crystals are filtered off with suction and washed with 5 ml of methyl tert-butyl ether. The crystals are dried at temperatures of less than 40° C. under reduced pressure. This gives 19.3 g of crystalline-[[(6-chloropyridin-3-yl) methyl](2,2-difluoroethyl)amino]furan-2(5H)-one having a melting point in the range of 72-74° C.

The $^1$H-NMR (CDCl$_3$, 298K) corresponds to that of amorphous 4-[[(6-chloropyridin-3-yl)methyl](2,2-difluoroethyl) amino]furan-2(5H)-one as indicated above.

Preparation Example 3

20 g of the amorphous 4-[[(6-chloropyridin-3-yl)methyl] (2,2-difluoroethyl)amino]furan-2(5H)-one are dissolved in 20 g of ethanol at 50° C. The mixture is then cooled to 40° C. and stirred at 40° C. for 16 h. The mixture is then cooled to 5° C. over a period of 4 h. The precipitated crystals are filtered off with suction and dried at temperatures of less than 40° C. under reduced pressure. This gives 17.2 g of crystalline-[[(6-chloropyridin-3-yl)methyl](2,2-difluoroethyl)amino]furan-2(5H)-one having a melting point in the range of 72-74° C.

The $^1$H-NMR (CDCl$_3$, 298K) corresponds to that of amorphous 4-[[(6-chloropyridin-3-yl)methyl](2,2-difluoroethyl) amino]furan-2(5H)-one as indicated above.

Preparation Example 4

20 g of 4-[[(6-chloropyridin-3-yl)methyl](2,2-difluoroethyl)amino]furan-2(5H)-one are dissolved in 20 g of 1-propanol at 50° C. The mixture is then cooled to 40° C. and stirred at 40° C. for 16 h. The mixture is then cooled to 5° C. over a period of 4 h. The precipitated crystals are filtered off with suction and dried at temperatures of less than 40° C. under reduced pressure. This gives 15.1 g of crystalline 4-[[(6-chloropyridin-3-yl)methyl](2,2-difluoroethyl)amino]furan-2(5H)-one having a melting point in the range of 72-74° C.

The $^1$H-NMR (CDCl$_3$, 298K) corresponds to that of amorphous 4-[[(6-chloropyridin-3-yl)methyl](2,2-difluoroethyl) amino]furan-2(5H)-one as indicated above.

FORMULATION EXAMPLES

1. Preparation of a Suspension Concentrate of the Novel Solid Form of 4-[[6-chloropyridin-3-yl)methyl](2,2-difluoroethyl)amino]furan-2(5H)-one To prepare a suspension concentrate, initially all liquid components and then the solids and the novel solid form of 4-[[(6-chloropyridin-3-yl)methyl](2,2-difluoroethyl)amino]furan-2(5H)-one are added to the water and stirred until a homogeneous suspension is formed. The homogeneous suspension is subjected first to coarse grinding and then to fine grinding in a bead mill, giving a suspension in which 90% of the solid particles have a particle size of less than 10 μm. Subsequently, a solution of Kelzan® S, (Kelzan® S comprises xanthan gum (CAS No. 11138-66-2) and glyoxal (CAS No. 107-22-2)) gum) and water is added with stirring at room temperature. A homogeneous suspension concentrate is obtained. During the preparation, it is made sure that the product temperature in the individual formulation steps does not exceed 40° C.

To test for storage stability, the suspension concentrate is stored at 40° C. for eight weeks. Subsequent examination of the chemical and physical properties showed only minor tolerable deviations of the values compared to the original values. Even after storage, applicability and activity of the product are not adversely affected.

2. Preparation of Water-Dispersible Granules of the Novel Solid Form of 4-[[(6-chloropyridin-3-yl)methyl](2,2-difluoroethyl)amino]furan-2(5H)-one To prepare water-dispersible granules, all solid ingredients of the recipe and the novel solid form of 4-[[(6-chloropyridin-3-yl)methyl](2,2-difluoroethyl)amino]furan-2(5H)-one are mixed in a mixer (for example a plough mixer with chopper) and pre-comminuted. The mixture of the solids is then subjected to air jet milling such that 90% of the solid particles have a particle size of less than 20 μm. About 15 of water are then incorporated into the mixture of the solids, with the mixer operated at high speed. The moistened mixture of the solids is then converted with minimum pressure and input of energy by a suitable extruder into product strands which, on exiting the matrix and during drying, disintegrate with formation of the rod-shaped water-dispersible granules. During the preparation, it is made sure that the product temperature in the individual formulation steps does not exceed 40° C.

To test for storage stability, the water-dispersible granules are stored at 40 C for eight weeks. Subsequent examination of the chemical and physical properties showed only minor tolerable deviations of the values compared to the original values. Even after storage, applicability and activity of the product are not adversely affected.

The invention claimed is:

1. A process for preparing a solid form of 4-[[6-chloropyridin-3-yl)methyl](2,2-difluoroethyl)amino]furan-2(5H)-one having a melting point of 65° C. to 75° C. comprising:
 (a) dissolving 4-[[(6-chloropyridin-3-yl)methyl](2,2-difluoroethyl)amino]furan-2(5H)-one in a solvent or solvent mixture at a temperature of at least 30° C. to form a crystallization solution, and
 (b) cooling the solution.

2. A process according to claim 1 where the cooling takes place in a step-wise manner.

3. A process according to claim 1 in which the solvent or solvent mixture is selected from the group consisting of isopropanol, toluene, methyl-THF, diethyl carbonate, chlorobenzene, n-butyl acetate and isobutyl acetate, n-butanol, ethanol, ethyl malonate, methyl t-butyl ether, and mixtures of toluene and butanol, of toluene and n-butyl acetate, of ethyl malonate and methyl t-butyl ether, and of butyl acetate and methyl t-butyl ether.

4. A process according to claim 1 wherein the solid form of 4-[[(6-chloro-pyridin-3-yl)methyl](2,2-difluoroethyl)amino]furan-2(5H)-one has a melting point in the range of 72° C. to 74° C.

5. The process according to claim 1 wherein the solid form of 4-[[(6-chloro-pyridin-3-yl)methyl](2,2-difluoroethyl)amino]furan-2(5H)-one is characterized by an X-ray powder diffractogram at 25° C. having the 2Θ (2 theta) values below:
 2Θ=16.8°
 2Θ=17.8°
 2Θ=20.2°
 2Θ=21.7°
 2Θ=23.6°
 2Θ=23.9°
 2Θ=24.7°
 2Θ=25.3°.

6. A process according to claim 1 wherein 4-[[(6-chloro-pyridin-3-yl)methyl](2,2-difluoroethyl)amino]furan-2(5H)-one is dissolved in step (a) at a temperature of at least 50° C.

7. A process according to claim 3 wherein the crystallization solution is stirred at about 40° C.

8. A process according to claim 7 wherein the crystallization solution is stirred at about 40° C. for 2 to 20 hours.

9. A process according to claim 7 wherein the crystallization solution is stirred at about 40° C. for 4 to 20 hours.

10. A process according to claim 7 wherein the crystallization solution is stirred at about 40° C. for 4 to 16 hours.

11. A process according to claim 1 wherein seed crystals are added to the crystallization solution.

12. A process according to claim 11 wherein seed crystals are added after stirring.

13. A solid form of 4-[[(6-chloropyridin-3-yl)methyl](2,2-difluoroethyl)amino]furan-2(5H)-one produced by a process according to claim 1.

* * * * *